United States Patent [19]

Cheetham

[11] 4,443,538
[45] Apr. 17, 1984

[54] STABILIZATION OF IMMOBILIZED ENZYMES WITH GLYCEROL

[75] Inventor: Peter S. J. Cheetham, Reading, England

[73] Assignee: Tate & Lyle Public Limited Company, London, England

[21] Appl. No.: 375,179

[22] Filed: May 5, 1982

[30] Foreign Application Priority Data

May 11, 1981 [GB] United Kingdom ................. 8114295

[51] Int. Cl.³ ......................... C12P 1/04; C12P 19/18; C12N 11/10; C12N 1/04
[52] U.S. Cl. ........................................ 435/41; 435/97; 435/170; 435/178; 435/182; 435/260
[58] Field of Search ............... 435/260, 174, 177, 178, 435/182, 41, 170

[56] References Cited

U.S. PATENT DOCUMENTS

| Re. 28,276 | 12/1974 | Farr ..................................... 435/260 |
| Re. 28,488 | 7/1975 | Farr ................................. 435/260 X |
| 2,938,794 | 5/1960 | Herman .............................. 435/260 |
| 3,730,841 | 5/1973 | Forgione et al. .................. 435/182 |
| 3,733,205 | 5/1973 | Shovers et al. ................. 435/178 X |
| 3,960,664 | 6/1976 | Olsen et al. ..................... 435/260 X |
| 3,975,545 | 8/1976 | Vedamuthu ..................... 435/260 X |
| 4,226,940 | 10/1980 | Storrs .................................. 435/260 |
| 4,246,349 | 1/1981 | Messing et al. ................. 435/260 X |
| 4,359,531 | 11/1982 | Bucke et al. .................... 435/178 X |

OTHER PUBLICATIONS

The Condensed Chemical Dictionary, 8th Ed., Van Nostrand Reinhold Co., N.Y. 1971, (pp. 420, 421 & 449).

*Primary Examiner*—David M. Naff
*Attorney, Agent, or Firm*—Ostrolenk, Faber, Gerb & Soffen

[57] ABSTRACT

Enzyme-containing cells immobilized in an alginate gel are stabilized by contacting the gel with glycerol in a ratio of cells to glycerol of 2:1 to 1:5. The enzyme-containing cells preferably convert sucrose to isomaltulose.

14 Claims, No Drawings

STABILIZATION OF IMMOBILIZED ENZYMES WITH GLYCEROL

BACKGROUND OF THE INVENTION

The present invention relates to the immobilization of enzymes.

Immobilized enzymes are becoming of increased industrial importance, particularly with the upsurge in interest in the subject popularly termed "biotechnology". In fact, immobilized enzymes have long been proposed as an efficient system for carrying out reactions catalysed by enzymes though there have been practical difficulties in achieving economic continuous operation.

To take one example, enzymes have been used in solution for many years for batch hydrolysis and thinning of starches in the production of glucose syrups. There have been many suggestions for ways in which the enzymes could be immobilized to permit continuous operation, but none of these suggestions has met with unqualified acceptance.

Apart from immobilization of enzymes themselves, various techniques have been put forward as ways in which the enzymes could be immobilized without isolation. In particular, whole cells of micro-organisms can be immobilized, thus using the cell as a carrier for the enzyme and obviating the need for extraction of the enzyme from the cell.

Of the immobilization techniques which I have tried for immobilization of cells, I find that immobilization by entrapment within a gel, especially an alginate gel, can give various advantages stemming from the fact that the cells are trapped in an inert, three-dimensional polymer network with relatively large interconnected interstitial spaces in the gel. More generally, other workers have reported on the usefulness of gel entrapment, especially entrapment in an alginate gel, as an immobilization technique.

One problem with gel-immobilized cells is a marked tendency for activity to be lost during storage or other periods of non-use, for instance during transportation. An accompanying difficulty during non-use is the tendency for contaminating micro-organisms to proliferate. It is a relatively routine matter to prepare gel-immobilized cells which have high activity upon immediate use, but the activity tends to decay relative quickly if the gel-immobilized cells are not used. The gel has a high water activity and probably provides a good environment for growth of contaminant moulds, bacteria and the like.

Operational stability and storage stability are useful concepts when reviewing the extent of any activity loss.

During operation of a conversion process using gel-immobilized cells, there is usually some progressive loss in the activity of the enzyme system. This decay can be slow, particularly if the cells are operating on a nutritionally deficieint medium which is inadequate for sustaining microbial growth. The loss in the activity can be assessed as a half-life, in the same way as radioactive decay. For instance, it might be that the activity of gel-immobilized cells is reduced by half during a period of use of say 2000 hours.

In a similar manner, it is possible to monitor any loss of activity while the gel-immobilized cells are not in use. Measurement of the activity before and after storage or other inactive period gives the activity loss, and the half-life obtained in this way can be called the storage half-life. In general, this storage half-life is less than the operational half-life.

Thus, it is often found that when freshly prepared gel-immobilized cells with high operational stability are not put into immediate use, the operational stability is much less at the time when the cells are eventually put into use. If gel-immobilized cells are stored at low temperatures, it sometimes adequate to store them in bottles covered with plastics wrap-film, but at higher (ambient) temperatures where fungal spores might be more plentiful this procedure is normally insufficient. Microbial growth, chiefly moulds, is typically observed. Consequently, the cells have to be stored in gas-tight tubes and only opened immediately before use. It will be appreciated that even when this mode of storage is successful, it is not a practical proposition for large-scale industrial use.

We have examined ways in which the immobilized cells could be stored, particularly with a view to developing a storage method which allows easy handling and transportation of the immobilized enzyme system. The conventional methods of preserving biological materials in the food industry include irradiation, dehydration, chilling, or the use of extremes of pH or osmotic pressure. However it is preferable to avoid excessive exposure to stresses such as extreme of temperature or pH, osmotic shock, and in particular composite stresses such as combinations of the above stresses, especially if a high storage stability is desired.

To give one specific example, freeze-drying frequently leads to an appreciable loss in activity and a short operational and storage half-life.

OBJECTS OF THE INVENTION

To summarise, the operational stability of freshly prepared gel-immobilized cells is often high, but there is a need for high storage stabilty as well. Coupled with this need is the requirement of high mechanical strength.

SUMMARY OF THE INVENTION

Exceptionally, it has now found that it is possible to contact with a particular dewatering agent a gel containing immobilized cells and obtain extended enzyme activity while achieving unexpected advantages.

It will be appreciated that an essential component of a gel is the water or other solvent system which constitutes up to 95% of the gel. The solvent gives the gel its characteristic physical properties, especially a high intra-gel volume through which molecules may diffuse during an enzymatic conversion process.

PREFERRED EMBODIMENTS OF THE INVENTION

In accordance with the present invention, process for preparing an immobilized enzyme system is provided, in which enzyme-containing cells are immobilized in a gel and then contacted with glycerol. The presence of the glycerol can impart high storage stabilities to the cells, without leading to detrimental effects.

Reflecting the enhanced storage stability of the immobilized cells, a method of storing and transporting gel-immobilized cells is also provided, wherein the cells are stored and/or transported in the presence of glycerol.

The effect of the glycerol is difficult to explain since analogues of glycerol do not appear to give the same benefits. Moreover, the effect is not simply one of modifying the water activity of the immobilized system.

In preparing gels of the invention, an enzyme system is immobilized by entrapment in a gel. The enzyme system can comprise one or a series of enzymes, and takes the form of the whole cells of one or more organisms such as yeasts or bacteria.

Of the available gel immobilization techniques, for the present process we prefer entrapment in an alginate gel. However, other suitable materials include polyacrylamide, agar, xanthan gum/locust bean gum, kappa-carrageenan or kappa-carageenan/locust bean gum. With an alginate gel, I find a calcium alginate gel gives best results. Other alginate gels can be used, such as those formed with other group II metals. For immobilization of an enzyme system in an alginate gel, we prefer first to mix the enzyme system with an aqueous solution of a soluble alginate, for example sodium alginate. The concentration in the mixture is in no way critical to the success of the present process, but by trying various concentrations an optimum can readily be found for a particular system. Equally, the concentration of soluble alginate is not critical.

The resultant enzyme system/alginate mixture is then metered into a solution of a metal salt with which the soluble alginate forms a gel. For the preferred calcium alginate gel, suitable salts include calcium chloride, especially a calcium chloride solution whose molarity is from 0.1 to 1 M.

By metering in the slurry as discrete droplets, it is a simple matter to produce spherical pellets of gel entrapping the cells. The pellet size can be varied, but it is preferred to generate pellets which are about 3 to 5 mm in diameter. However, the size and shape is of limited consequence, and it is readily possible to immobilize the cells in a block of gel or in a rope of gel.

Similar techniques can be used for immobilizing the cells in other gel systems. Procedures for forming gelled products are available in the literature, and it is a simple matter to adapt them to the present purposes.

If desired, the cells can be co-immobilized with other materials, particularly but not exclusively inert materials. Preferably any inert material which is used consists of particles with dimensions of from 250 to 1500 micron. A maximum dimension less than about 150 micron is undesirable if the product is to be used in a fluidized bed reactor.

Examples of inert materials which can be used include porous particles of either naturally-occurring or manufactured materials.

Bone char, otherwise known as bone black, bone charcoal or animal charcoal, is a particularly suitable inert material for the present invention and offers a combination of advantageous properties which is not met by other materials.

Bone char is obtained at an economically favourable cost from a naturally-occurring raw material, and consists principally of a hydroxyapatite structure over which there is a thin, evenly-dispersed coating of active carbon, with the particles being of an irregular form and providing a suitable 'key' for adhesion of the external deposit. In addition, it has been used for many years in sugar refining throughout the world, and it is well established that its use entails no hazardous problems in the food industry. It exhibits a good degree of thermal stability and ordinarily contains no artificial additives which might give rise to further problems even when used in mildly acidic conditions.

The particle size of the bone char is not critical for a successful immobilization. I prefer to use particles with a minimum dimension of less than 2 mm, more preferably less than 1 mm, and with a maximum dimension of less than 6 mm, more preferably less than 2 mm.

After formation of the gel-immobilized enzyme system, the gel is optionally dried. The drying technique is not particularly critcal, though simple air drying at or near room temperature using a current of air appears to give the best results. Drying the gel to less than 70% of its original volume, for example to less than 40% of its original volume is particularly suitable. It is preferred to dry off only the gel-associated water, and to leave behind the cell-associated water.

Despite the loss of water occasioned by the drying, the dried, enzyme-containing gels retain enzyme activity. Often the activity of the gel will be less after drying when expressed in terms of amount of substrate which is converted in unit time by a given sample of gel. On the other hand, the reduction in gel volume will usually mean that the activity per unit volume will be greater after drying. Some uptake of water may occur when the dried gels of the invention are used to effect an enzyme-catalysed reaction in aqueous solution, but normally some reduction in gel volume is maintained. Thus the increase in activity per unit volume is normally maintained.

Apart from retention of enzyme activity, the dried gels of the invention have other beneficial properties. Thus, they are typically stronger, more resistant to compression and abrasion, and easier to handle and to transport.

Air drying is suitably effected at 20° to 50° C. for 10 to 200 hours, with 50 to 150 hours at 30° to 35° C. representing preferred conditions. Gentle turning over of the gel during drying is helpful, as also is the use of air with low humidity.

The dried gel preferably has a volume less than 70% of that of undried gel, and preferably weighs less than 70% of the undried gel.

The retention of enzymatic activity after drying is sometimes enhanced if the gel contains a solute or substrate. Such additives can also be used to modify the stability of the dry product, and may be incorporated during the formation of the gel. To give one example, sucrose is a solute which can beneficially be added to the metal salt solution (usually a calcium salt) during formation of an alginate gel.

Following the preparation of the gel and the optional drying, the immobilized cells are contacted with glycerol. For preference, the glycerol is used in a ratio of from 5:1 to 1:30, expressed as kilograms of cells per litre of glycerol, though other ratios are possible. In practice with alginate gels, I prefer to use a ratio of from 2:1 to 1:5, more usually about 1:1. In simple terms, it is often appropriate to add enough glycerol to cover the immobilized cells. The cells are then suitable for storage and handling in the glycerol environment. The storage stability can be further improved if the cells are stored at below ambient temperature.

The high storage stabilities achieved when immobilized cells are immersed in or otherwise contacted with glycerol is surprising since closely similar compounds do not appear to give the same effect.

For use, the gel-immobilized enzyme system is contacted with a substrate solution, thereby effecting the desired enzymatic conversion. If necessary, the glycerol can be decanted off or otherwise removed before the contacting step. The contacting with substrate solution is preferably performed as part of a continuous process, using for instance a column loaded with pellets of the enzyme-containing gel and through which column the solution is passed. The converted solution is then recovered and can be processed in conventional manner.

EXAMPLES OF THE INVENTION

The present invention is illustrated by the following non-limiting Examples. Comparative Examples are also given.

In the examples employing cells of *Erwinia rhapontici*, the activity was assessed using standardized procedures for the conversion of sucrose to isomaltulose. In one standardized procedure for continuous operation, the immobilized enzyme system was packed in a jacketed column (30 cm tall, 5 cm diameter). A solution of sucrose 55% (w/v) in deionised water was prepared and adjusted to pH 7.0 with 1.0 M NaOH. The sucrose solution was pumped up the column, which was maintained at 30° C. With the sucrose flow rate at approximately 0.1 empty column volumes/hour (ecv/h), coversion of sucrose to isomaltulose approached equilibrium. The product stream was then analysed to give the activity of the immobilized enzyme system: this activity can usefully be considered either in terms of grams of product per gram of wet cells per hour, that is, g/gc/h, or in terms of grams of product per gram of pellets per hour, that is, g/gp/h. In another standardized procedure for batch operation and suited for experiments on a small scale, the activity was determined with a simple routine involving shaking the pellets in the substrate solution at 30° C. for about 15 hours and analysing the resultant solution: such a determination gave the activity in a simple manner.

COMPARATIVE EXAMPLE 1

Preparation of immobilized enzyme system

Cells of *Erwinia rhapontici* NCPBB 1578 were suspended in a solution of sodium alginate (5% dry wt/v) in deionised water so as to form a 20% wet wt/v suspension of cells. The cell suspension was then extruded dropwise from a height of 10 cm into a stirred solution of calcium chloride (0.1 M) maintained at 30° C. The resulting pellets were stirred for one hour and then filtered off.

Assay of the freshly prepared pellets under continuous operation showed that in this instance they had an activity of about 0.4 g/gc/h when the substrate conversion was 100% to product. Continuous use of the pellets by continuous running of the column showed that the activity was decaying to half in about 8500 hours. Thus, the half-life of the pellets when used immediately after preparation was about 8500 hours.

While the half-life of this particular sample of immobilized enzyme system was about 8500 hours when used straight away for continuous conversion of the 55% sucrose solution, the pellets deteriorated relatively rapidly on attempted storage.

Generally there was appreciable loss of activity and often evidence of contaminant microbial growth whenever samples of the pellets were no being used for any length of time (say several days or more). The conditions possibly favour contaminant growth; the water activity ($a_w$) of the pellets when freshly prepared was 1.00. When the pellets were stored at 18° C. it was often sufficient to store them in bottles covered with plastics wrap-film, but at higher ambient temperatures where fungal spores might be more plentiful this procedure was insufficient. Microbial growth, chiefly moulds, was usually observed on the surface of the pellets within approximately 200 hours.

Consequently, the pellets had to be stored in gas-tight tubes and only opened immediately before use. It will be appreciated that this mode of storage is not a practical proposition for large-scale industrial use. Moreover, the centrifuged pellets when stored under these conditions had a storage half-life of only 124 hours. Similarly, the cells when stored as the alginate slurry had a storage half-life of only 101 hours.

In many experiments, I tried to find ways in which the pellets could be stored, particularly with a view to developing a storage method which allows easy handling and transportation of the immobilized enzyme system.

In particular, the pellets were stored under twice their volume of the 55% sucrose solution at 20° C. for 500 hours, and the activity again determined. In this way it was found that the storage half-life for the decay in activity during the period of storage under 55% sucrose solution was only about 120 hours. Furthermore, the storage stability under saturated sodium chloride was only 250 hours.

After the determination of the activity following storage under sucrose solution, the pellets were filtered off and reweighed. It was found that the pellets had gained 216% in weight due to uptake of liquid.

Moreover, freeze-drying of the pellets led to an appreciable loss in the activity and a short half-life of around 125 hours. Thus, freeze-drying gave pellets whose activity will fall by half in about 5 days. Clearly this loss in activity is unacceptable for storage, handling and transportation of the prepared pellets.

To summarise, the operational stability of the freshly prepared pellets is high, but there is a need for high storage stability as well.

EXAMPLE 1

Contacting with glycerol

About 50 g of the freshly prepared pellets of Comparative Example 1 were placed in a beaker and about two volumes of Analar (trade mark) glycerol (at least 99% pure), relative to the pellet volume, was poured in. The pellets were then stored at about 20° C. under the glycerol for 500 hours or more. The activity was thereafter assayed: it was found that the half-life during storage under glycerol was about 1100 hours.

After the determination of the activity following storage under glycerol, the pellets were filtered off and reweighed. It was found that the pellets had not gained in weight. Even after 60 hours of use following the storage under glycerol, there was no weight gain.

EXAMPLE 2

Drying and then contacting with glycerol

About 50 g of the freshly prepared pellets of Comparative Example 1 were dried as a monolayer and under constant agitation at 30° C. in a well-ventilated environment. The drying was carried out until the pellets were 44% of their original volume.

The dried pellets were then stored under glycerol in the same way as in Example 1. The activity was thereafter assayed: it was found that the half-life during storage under glycerol was about 850 hours. Nevertheless, when assessed on a weight basis, the pellets after storage were more active then those of Example 1 after storage for the same length. In other words, the activity in g/gc/h after storage was lower than for the stored pellets of Example 1 but the activity in g/gp/h was higher.

The pellets were also weighed to determine any liquid uptake upon exposure to the 55% sucrose solution. As in Example 1, it was found that the pellets had not gained in weight, even after 60 hours of use.

Some further experiments were carried out in which the drying conditions were varied. The degree to which the pellets had to be dried before reaching maximum activity was inversely proportional to the cell loading, presumably because removal of cell-associated rather than support-associated water has a marked denaturing effect. Thus when the pellets contained 20% (wv/v) cells the highest activities were recorded after drying to 35% of the pellets original volume. Drying of pellets was also advantageous in that the pellets were then stronger and so more resistant to compression in packed columns or abrasion in stirred reactors and were easier to transport and handle. They were less bulky and more even-flowing than the pellets of Example 1.

An additional advantage of the inclusion of the drying step is that because the density is slightly greater than that of the pellets which have not been dried, the pellets of this Example 2 are more suited to use in fluidized bed reactors.

EXAMPLE 3

Contacting with various ratios of glycerol

The water activity ($a_w$) of the glycerol filtered off in the procedures of Examples 1 and 2 was determined. For Example 1, the $a_w$ was 0.78 and for Example 2, it was 0.73. Thus, the glycerol had extracted water from the pellets.

It is generally held that a water activity below around 0.6 is required to prevent microbial growth. Accordingly, increasingly greater amounts of glycerol were employed with the expectation that this would further lower the water activity to the point where prolonged stability of the stored immobilized enzyme system was obtained.

In the same way as in Example 1, samples of about 50 g of the freshly prepared pellets of Comparative Example 1 (activity 0.39 g/gc/h) were placed in respective beakers and glycerol in the amounts shown in the next Table was poured in. The pellets were then stored at about 20° C. under the glycerol for around 500 hours and the activity assayed, giving the results shown.

TABLE

| Contacting with various ratios of glycerol | | | |
|---|---|---|---|
| Ratio of glycerol:pellets (g:ml) | Activity after storage (g/gc/h) | Relative activity (as % of pre-storage) | Storage stability ($t^{-0.5}$h) |
| 1:1 | 0.4 | 102 | infinity |
| 1:2 | 0.35 | 90 | 2500 |
| 1:3 | 0.25 | 64 | 700 |
| 1:5 | 0.15 | 38 | 410 |
| 1:10 | 0.27 | 69 | 820 |

Contrary to expectations, and for some reason which is not apparent, the relative activity and storage stability fell when the relative amount of glycerol was raised to the ratio of 1:5. Thereafter the relative activity and storage stability increased upon altering the ratio to 1:10.

COMPARATIVE EXAMPLE 2

Contacting with various analogues of glycerol

Following the results of Examples 1 to 3, and particularly after the unexpected result of Example 3, other compounds were assessed for their ability to enhance the storage stability of the immobilized enzyme system prepared in accordance with the technique of Comparative Example 1. Analogues of glycerol were chosen and employed at a ratio of 1:1 g:ml but otherwise in the same way as in Example 1 using freshly prepared samples of pellets whose initial activity before storage was as shown in the Table. The results shown in the following Table were obtained.

TABLE

| Contacting with various analogues of glycerol | | | |
|---|---|---|---|
| | Pettet activity (g/gc/h) | | |
| Analogue of glycerol | Before storage | After storage | Relative activity (%) |
| ethylene glycol | 0.87 | 0.09 | 10 |
| butanediol | 0.87 | 0 | 0 |
| hexylene glycol | 1.09 | 0.09 | 8 |
| 1,3-propanediol | 0.78 | 0.11 | 14 |
| polyethylene glycol | | | |
| mw 100 | 0.37 | 0 | 0 |
| mw 200 | 0.37 | 0 | 0 |

The analogues are seen to give bad results, which is surprising particularly since some of them are recognized to possess a preservative action. As with Example 3, it is seen that the effect of the glycerol is not easily rationalized.

EXAMPLE 4

Contacting with glycerol and bacteriostatic agent

The procedure of Comparative Example 1 was repeated to give freshly prepared pellets, except that a bacteriostatic agent was added to the alginate solution, the calcium chloride solution and the glycerol at the level indicated in the following Table. The bacteriostats were commercially available materials comprising (i) the materials identified by the trade mark Nipa and believed to be esters of benzoic acid derivatives; (ii) penicillin G; and (iii) chloramphenicol. The pellets were stored under glycerol (at a ratio of 1:1 g:ml) in a similar manner to Example 1. The results are shown in the following Table.

TABLE

| Contacting with glycerol and bacteriostatic agent | | | |
|---|---|---|---|
| | Pellet activity (g/gc/h) | | Relative activity (%) |
| Bacteriostat | Before storage | After storage | |
| 0.06% Nipasept Na | 1.00 | 0.65 | 55 |
| 0.01% Nipacombin A | 1.00 | 0.60 | 60 |
| 0.0125% Nipaheptyl | 1.00 | 0.84 | 84 |
| 1.76 mmg/ml penicillin G | 0.56 | 0.67 | 120 |
| 1.76 mmg/ml chloramphenicol | 0.56 | 0.54 | 96 |

In each case, the storage stability of the immobilized enzyme system was very high. Similar experiments were carried out but including drying to about 45% of the original weight as in Example 2. The storage stability was again very high.

EXAMPLE 5

Drying and contacting with glycerol and bacteriostatic agent

The procedure of Example 4 was repeated, except that the drying step of Example 2 was also included. Moreover, the level of glycerol was varied. The conditions and results are shown in the following Table which comes in two parts. The initial activity of the freshly prepared pellets was 0.57 g/gc/h and the initial activity of the dried pellets was 0.25 g/gc/h.

TABLE (part 1)

Drying, contacting with glycerol and bacteriostatic agent

| Bacteriostat | Pellet: gycerol ratio (g:ml) | Activity after storage (g/gc/h) | Storage stability (half-life (h) |
|---|---|---|---|
| None | 1:1 | 0.32 | infinity* |
| None | 1:3 | 0.26 | infinity |
| 0.06% Nipasept Na | 1:1 | 0.15 | 810 |
| 0.06% Nipasept Na | 1:3 | 0.31 | infinity |
| 0.01% Nipacombin A | 1:1 | 0.12 | 620 |
| 0.01% Nipacombin A | 1:3 | 0.25 | infinity |
| 0.0125% Nipaheptyl | 1:1 | 0.23 | 4050 |
| 0.0125% Nipaheptyl | 1:3 | 0.25 | infinity |

*infinity: within the period of the storage test there was no loss of activity.

TABLE (part 2)

Drying, contacting with glycerol and bacteriostatic agent

| Bacteriostat and pellet: glycerol | Weight of pellets (% of undried) | | |
|---|---|---|---|
| | After drying, before glycerol | After storage (for 505h) | After storage and use |
| None; 1:1 | 43.1 | 29.0 | 27.7 |
| None; 1:3 | 43.1 | 29.4 | 25.8 |
| Nipasept Na; 1:1 | 45.2 | 38.5 | 37.3 |
| Nipasept Na; 1:3 | 45.2 | 35.0 | 37.1 |
| Nipacombin A; 1:1 | 47.8 | 44.0 | 42.5 |
| Nipacombin A; 1:3 | 47.8 | 40.5 | 42.2 |
| Nipaheptyl; 1:1 | 43.2 | 36.3 | 34.8 |
| Nipaheptyl; 1:3 | 43.2 | 32.8 | 34.0 |

It can be seen that high storage stabilities with low weight regain properties are generally obtained.

EXAMPLE 6

Use of other strains

The procedure of Example 1 was repeated using other strains of the microorganism, and gave the results shown in the following Table.

TABLE

| Deposited Strain | Use of other strains Pellet activity (g/gc/h) | | |
|---|---|---|---|
| | Before storage | After storage | Relative |
| NCPPB 1739 | 0.78 | 0.6 | 77 |
| NCPPB 139 | 0.71 | 0.59 | 83 |
| ATCC 29284 | 0.88 | 0.93 | 106 |

The stability of the ATCC strain under storage is most unexpected since under conventional continuous use immediately after preparation there is a rapid decline in activity.

More generally, experiments with other organisms showed the broad applicability of the present invention. For example, cells of *Serratia marcescens* NCIB 8285, *Serratia plymuthica* ATCC 15928 and *Protaminobacter ruber* NCIB 2879 were immobilized by the procedure of Comparative Example 1 and successfully stored under glycerol before being used in conventional manner to convert sucrose.

I claim:

1. A process for preparing an immobilized enzyme system, said process comprising the steps of immobilizing enzyme-containing cells in an alginate gel and then contacting said gel with glycerol in a ratio of from 2:1 to 1:5, expressed as kilograms of cells per liter of glycerol.

2. The process of claim 1, wherein after said step of immobilizing said cells and before said step of contacting said gel with glycerol, said gel is dried.

3. The process of claim 2, wherein drying is effected at about room temperature using a current of air.

4. The process of claim 3, wherein said gel is dried to less than 70% of its original volume.

5. The process of claim 1, wherein after said step of contacting said gel with glycerol, the gel is stored.

6. The process of claim 1 in which said ratio is about 1:1.

7. The process of claim 4 in which said ratio is about 1:1.

8. The process of claim 1 in which a bacteriostatic agent is added to said gel.

9. A method for extending the storage stability of alginate gel-immobilized cells containing an enzyme system, wherein said gel-immobilized cells are contacted with glycerol in a ratio of from 2:1 to 1:5, expressed as kilograms of cells per liter of glycerol.

10. A method for enzymic conversion of a substrate using alginate gel-immobilized cells in which method said cells are cells which have been stored and/or transported in admixture with glycerol in a ratio of from 2:1 to 1:5, expressed as kilograms of cells per liter of glycerol.

11. An immobilized enzyme system comprising an alginate gel having enzyme containing cells immobilized therein, in admixture with glycerol in a ratio of from 2.1 to 1:5, expressed as kilograms of cells per liter of glycerol.

12. The immobilized enzyme system of claim 11 in which said ratio is about 1.1.

13. The immobilized enzyme system of claim 11 in which said gel is in the form of pellets of about 3-5 mm in diameter.

14. The immobilized enzyme system of claim 11 which contains a bacteriostat.

* * * * *